(12) United States Patent
Romero Mejia et al.

(10) Patent No.: US 8,980,842 B2
(45) Date of Patent: Mar. 17, 2015

(54) **CONTRACEPTIVE PEPTIDES DERIVED FROM THE VENOM OF THE SPIDER *LATRODECTUS MIRABILIS*, NUCLEOTIDE SEQUENCES TO TRANSFORM A MICROORGANISM TO PRODUCE SAID PEPTIDES; METHODS TO OBTAIN THE PEPTIDES; PHARMACEUTICAL COMPOSITIONS CONTAINING THEREOF AND USE THEREOF**

(75) Inventors: Fernando Romero Mejia, Temuco (CL); Raúl Sanchez Gutierrez, Temuco (CL); Eduardo Bustos Obregón, Santiago (CL); Antonio De Miranda, Sao Paulo (BR); Andrés Rudolphy Fontaine, Santiago (CL)

(73) Assignees: Universidad de la Frontera (CL); Universidad de Chile (CL); Universidad Federal de Sao Paulo (BR); Laboratorios Andromaco S.A. (CL)

( * ) Notice: Subject to any disclaimer, the term of this patent is extended or adjusted under 35 U.S.C. 154(b) by 593 days.

(21) Appl. No.: 13/053,751

(22) Filed: Mar. 22, 2011

(65) Prior Publication Data

US 2011/0237523 A1    Sep. 29, 2011

(30) Foreign Application Priority Data

Mar. 23, 2010 (CL) .................................... 261-2010

(51) Int. Cl.
*A61K 38/10* (2006.01)
*C07K 14/435* (2006.01)
*A61K 38/00* (2006.01)

(52) U.S. Cl.
CPC ........... *C07K 14/43518* (2013.01); *A61K 38/00* (2013.01)
USPC ........................................ 514/21.4; 530/300

(58) Field of Classification Search
None
See application file for complete search history.

(56) References Cited

U.S. PATENT DOCUMENTS

| | | |
|---|---|---|
| 6,897,291 B1 | 5/2005 | Salkoff et al. |
| 2004/0157292 A1 | 8/2004 | Chapham et al. |
| 2006/0257868 A1 | 11/2006 | Moran et al. |
| 2007/0105188 A1 | 5/2007 | Travis et al. |
| 2009/0104604 A1 | 4/2009 | Ren et al. |
| 2009/0249499 A1 | 10/2009 | Moran et al. |

FOREIGN PATENT DOCUMENTS

| | | | |
|---|---|---|---|
| AU | 772403 | | 10/2000 |
| EP | 0 448 464 | | 9/1991 |
| WO | WO2009/083808 | * | 7/2009 |

OTHER PUBLICATIONS

Romero et al., Fertility and Sterility, 2007; 87: 1345-1349.*
Parodi et al., Biochemical and Biophysical Research Communications, 2008; 375: 571-575.*
Ambrósio et al. (XL Annual Meeting of Brazilian Biochemistry and Molecular Biology Society; Foz do Iguacu, PR, Brazil, Apr. 30th to May 3rd, 2011; 2 pages.*
Reddy et al. "Antimicrobial peptides: premises and promises." *Int. J. of Antimicrobial Agents*. vol. 24. 2004. pp. 536-547.
Yeung et al. "Effects of the ion-channel blocker quinine on human sperm volume, kinematics and mucus penetration, and the involvement of potassium channels." *Molecular Human Reproduction*. vol. 7. No. 9. 2001. pp. 819-828.

* cited by examiner

*Primary Examiner* — Christina Borgeest
(74) *Attorney, Agent, or Firm* — Merchant & Gould P.C.

(57) ABSTRACT

The present invention is directed to an active agent with contraceptive properties which corresponds to a peptide fragment of the *Latrodectus mirabilisi's* venom. The peptide generally includes the amino acid sequence of SEQ ID NO 2 or sequences that are at least 85% similar, obtained by chemical synthesis or through recombinant DNA technologies. Furthermore, a pharmaceutical contraceptive composition comprising the peptide fragment and one or more pharmaceutically acceptable vehicles is also described. The peptide fragment and pharmaceutical compositions are useful as a contraceptive and spermicide agent.

10 Claims, 3 Drawing Sheets

FIGURE 1

| | 1 5 10 15 20 25 30 35 40 45 50 55 60 65 69 |
|---|---|
| $ATX_{1-69}$ | ZDSLDPAEFACADDIDQAELLKNNDICLQCEDLHKEGLVFSLCKTNCFSTEYFQHCVKDLEEAKKEPPE |
| | PM = 7843,7009 |
| $[Cys(Acm)^{11}]-ATX_{1-24}-NH_2$ | ZDSLDPAEFAC(Acm)ADDIDQAELLKNN-$NH_2$ PM = 2687,8584 |
| | |
| $Ac-[Cys(Acm)^{11}]-ATX_{25-58}-NH_2$ | Ac-DICLQCEDLHKEGLVFSLCKTNC(Acm)FSTEYFQHCVK-$NH_2$ PM = 4089,7124 |
| | |
| $Ac-[Ala^{42}]-ATX_{41-60}-NH_2$ | Ac-SLAKTNCFTTEYFQHCVKDL-$NH_2$ PM = 2387,7232 |
| | |

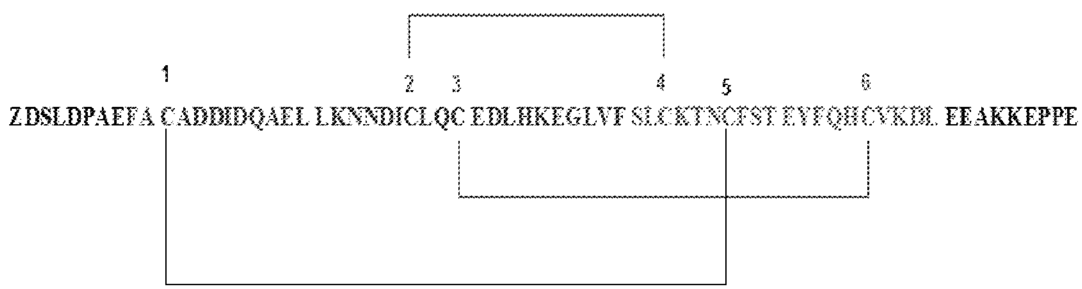

CONTRACEPTIVE PEPTIDES DERIVED FROM THE VENOM OF THE SPIDER *LATRODECTUS MIRABILIS*, NUCLEOTIDE SEQUENCES TO TRANSFORM A MICROORGANISM TO PRODUCE SAID PEPTIDES; METHODS TO OBTAIN THE PEPTIDES; PHARMACEUTICAL COMPOSITIONS CONTAINING THEREOF AND USE THEREOF

This application claims benefit of Serial No. 261-2010, filed 23 Mar. 2010 in Chile and which application is incorporated herein by reference. To the extent appropriate, a claim of priority is made to the above disclosed application.

FIELD OF THE INVENTION

The present invention is directed to peptides with contraceptive activity. In particular, the peptides are obtained from molecular fractions of the venom from the spider *Latrodectus mirabilis*.

BACKGROUND OF THE INVENTION

Contraception consists in the use of different methods to prevent fecundation or pregnancy when having sexual intercourse. Currently, there are different methods to avoid fecundation, which can be classified into barrier methods and chemical or hormonal methods.

Spermicides, which are chemical compounds that kill or inactivate spermatozoa, are one of the most prominent members of the chemical methods.

Spermicides, from a physiological point of view, must affect spermatozoid motility or by affecting the capacitive response, altering the membrane potential by blocking specific currents of any ionic species relevant to complete sperm maturation (such as calcium), blocking progesterone receptors or receptors of substances that act as chemotactic components for the spermatozoid.

One of the spermicides that have been used in some countries is Nonoxynol-9, a bioorganic molecule that exerts its action mainly as a biodetergent for membrane structures. It causes a partial digestion of the lipids that form the membrane barrier. In this way, the biodetergent cause micropores to form on the membrane, destroying the barrier that separates the intracellular and extracellular spaces, which finally establishes a transmembrane thermodynamic equilibrium that causes cell death. The pharmaceutical forms of Nonoxynol-9 comprise being used as an additive to barrier contraceptive methods (condom), as part of a lubricant and spermicide; vaginal ovules containing 168 mg of the substance; contraceptive sponges with 1,000 mg of the substance; lubricant gels for vaginal use and vaginal diaphragms. The side effects of this molecule have made the Food and Drug Administration (FDA) of the United States of America to reject the approval for use. These undesired effects are produced because Nonoxynol-9 causes clinical settings of irritation, inflammation and keratosis in other cellular tissues (vaginal mucose, cervix and lining membranes of labium majus and labium minor in women, and surface of the lining epithelium of the glans and the lining epithelium of the urinary meatus in men). Hence, when the molecule is applied to the genital zone of one or both members of the couple, the probability of infection with a Sexually Transmitted Disease (STD) is increased, as some WHO reports have linked the repeated use of Nonoxynol-9 with urinary tract infections. For example, lubricant gels have been designed to be used intravaginally.

However, some people use these gels intrarectally, which could promote disruption of the rectal epithelium due to the presence of Nonoxynol-9. (Phillips D M et al. 2000)

Spermicides can be natural of synthetic. A natural spermicide example is gossypol. Since 1950, gossypol was extracted in China from cottonseeds. This product is a potent male contraceptive since it inhibits competitively the lactic dehydrogenase enzyme, which is important in sperm cell production. It was used at concentrations from 75 to 100 μg twice a month. The problem associated with this molecular structure was that it caused chemical sterilization in the subjects, and therefore it could not be patented as a chemical spermicide, and it further caused hypokalemia, effects in the digestive system, fatigue and paralysis in extreme cases.

The work of Reddy et al., “Antimicrobial peptides: premises and promises” International Journal of Antimicrobial Agents 24 (2004) 536-547, describes the potential use of antimicrobial peptides as contraceptives that alter the ion flux through spermatozoid membranes. This work mentions magainin-A and nisin as examples of such peptides. However, no reference was made about natural or synthetic analog peptides obtained from a fraction of the *Latrodectus mirabilis* venom.

Yeung et al., in “Effects of the ion-channel blocker quinine on human sperm volume, kinematics and mucus penetration, and the involvement of potassium channels” Molecular Human Reproduction Vo1.7, No. 9 pp. 819-828, 2001, describe the effects of quinine on different ionic channels, particularly the consequences on cellular volume. They mention that said channels could be the targets of potential contraceptives, but no application examples are presented and no suggestions about other peptides with a similar action are made. Particularly, extracts from the *Latrodectus mirabilis* venom are not mentioned.

The patent application EP448464A1 describes a method to determine if a spermatozoid suffers the acrosomal reaction, using proteins C3, C3b or iC3, or fragments thereof. This document describes that antibodies against said proteins or protein fragments could be used as male or female contraceptive vaccines. Even though this document mentions peptide or protein alternatives, its objective is the creation of a contraceptive vaccine, which differs from the present invention, which is related to a spermicide based on extracts from the *Latrodectus mirabilis* venom or a synthetic peptide based on the nucleotide sequences obtained from said extract.

The U.S. Pat. No. 6,897,291B1 describe ionic channels that can be used to identify molecules that could potentially be used as contraceptives, however this document does not describe new contraceptive or spermicide molecules, but only a method to identify said molecules.

The Australian Patent AU772403B2 describe polypeptides based on FSP95, a protein that is located in the spermatozoid tail and has a function in sperm motility once the spermatozoid has been capacitated. The use of said polypeptides with contraceptive methods is mentioned, however, no information regarding their effectiveness is provided in said publication, since no biological data are described.

The US Patent Applications US20040157292-A1, US20090104604-A1, US20060257868-A1, US20090249499-A1, describe different ionic channels (CatSper1, CatSper2, CatSper3, CatSper4, respectively). Said channels are used to diagnose infertility, and all documents mention the use of preparations containing inhibitors of said channels as possible contraceptives. Particularly, antibodies against said ionic channels are mentioned, but no contraceptive peptides are suggested or mentioned.

The US Patent Application US20070105188A1 describes methods to identify potential contraceptive molecules, but do not describe such molecules.

In conclusion, there is no peptide, organic or immunological inhibitor molecule in the current state of the art that presents spermicidal properties and that could be used to prepare a viable pharmaceutical product to inhibit spermatozoa.

BRIEF DESCRIPTION OF THE DRAWINGS

FIG. 1. Amino acid sequence of the wild-type peptide (top; $ATX_{1-69}$ (SEQ ID NO:1) and three synthetic analogs ([Cys(Acm)$^{11}$]-$ATX_{1-24}$-$NH_2$ (SEQ ID NO:5); Ac-[Cys(Acm)$^{47}$]-$ATX_{25-58}$-$NH_2$ (SEQ ID NO:6); Ac-[Ala$^{43}$]-$ATX_{41-60}$-$NH_2$ (SEQ ID NO:2)) designed from said peptide. The third row, named Ac-[Ala$^{43}$]$ATX_{41-60}$-$NH_2$, shows the sequence of the analog with spermicidal activity that was used to perform the sperm motility assays, which sequence is presented in SEQ ID NO: 2.

DETAILED DESCRIPTION

Figure 2:
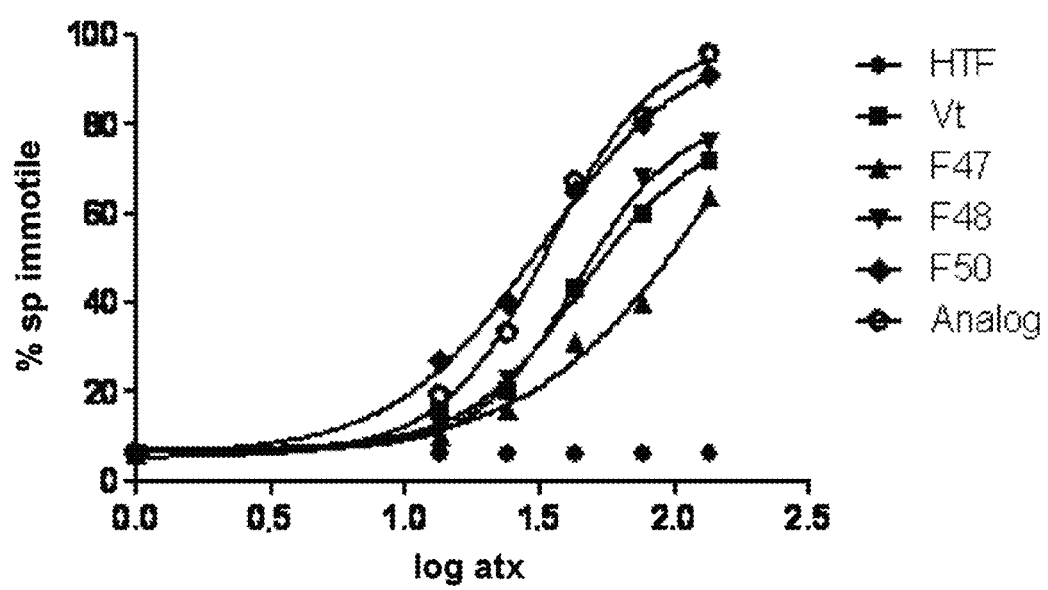
FIG. 2. Immobilizing effect of the total venom (Vt), fractions (F) and the designed analog, in selected human spermatozoa (swim up), incubated for 45 minutes in HTF medium. (Log atx: logarithm of the concentration (in mg/ml) of the assayed spermicidal agent). The 1050 for the analog is 39.81 μg/ml. The 1050 for the total venom is 17.8 μg/ml.
Figure 3:
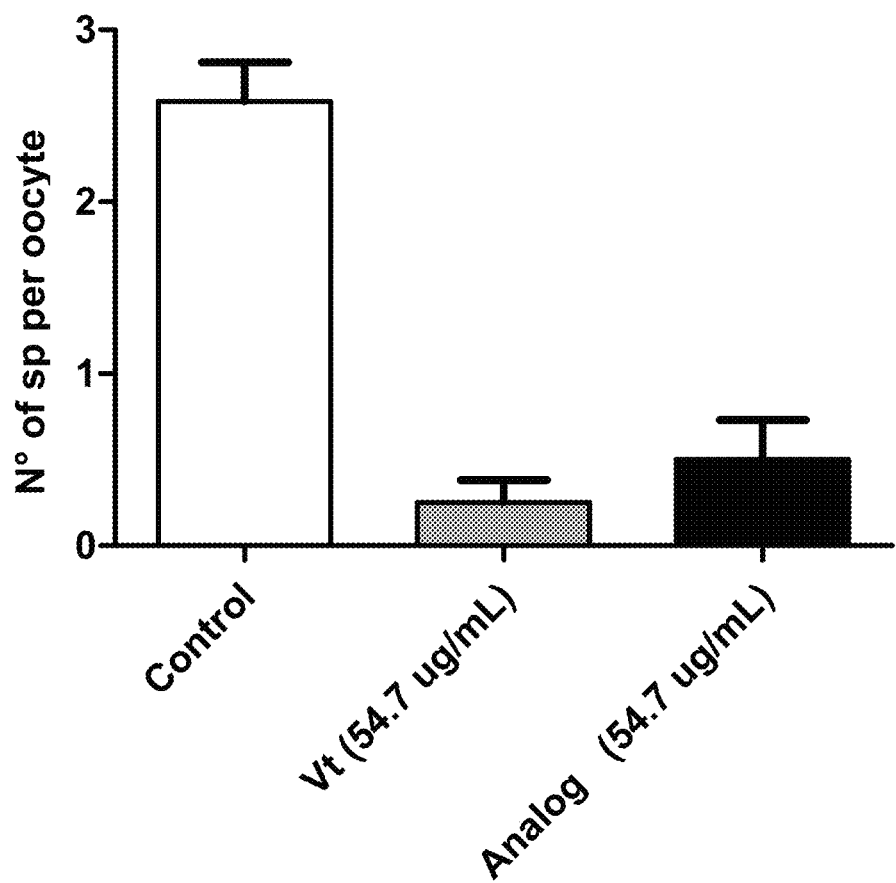
FIG. 3. Plot showing the number of human spermatozoa (sp) that are fusioned in the striated membrane of a female gamete (hamster oocyte). The technique of Yanagimachi et al. (1976) was used, which consists in an isolated method to test spermatozoid fertility. Three replicates with 5 oocytes per group were made each time (n=15 oocytes per group); the mean number of spermatozoa impacting the striated membrane of the oocytes was 2.75 in the control (hollow bar), and when a medium containing total venom (grey bar) or peptide analog (black bar) were put into the sperm fluid, the number of adhered spermatozoa is inferior to 1 for the same population of oocytes used in the experiments. This demonstrates a clear decrease of 90±0.1% and 82±0.3% in the fertilizing capacity of spermatozoa in the presence of total venom and the peptide analog, respectively. The concentrations used in the experiment were the IC50 previously calculated from the progressive sperm motility dose-response curve (FIG. 2).

In order to better understand the description of the present invention, a non-capacitated spermatozoid is an inert cellular gamete that has to undergo biochemical and electrophysiological changes in a transformation process from inert cell to functional cell, a process known as capacitation.

The present invention is related to molecular fractions obtained from the venom from the spider *Latrodectus mirabilis* (common name: black widow or red-belly spider). Said molecular fractions have made possible to develop a line of synthetic peptide products with biopharmaceutical action, inducing biochemical and electrophysiological changes that affect the mature ejaculated spermatozoid by modifying its fertilizing capacitation potential (preventing the spermatozoid to be capacitated). Therefore, said biopharmaceutical action corresponds to a contraceptive action, wherein the fertility response of the human sperm is inhibited.

The active principle of the contraceptive of the present invention induces biochemical modifications in the spermatozoa, related to intracellular pH changes, modification in the intracellular nitric oxide production levels, induction of changes in the intracellular concentration of $Ca^{2+}$, modification of the mitochondrial potential and the membrane potential, and modification of the intracellular potassium and calcium ionic currents.

The peptide spermicide, corresponding to a modification of a peptide found in a molecular fraction of the *Latrodectus mirabilis* venom, is an easily synthesizable low-molecular weight compound (2837 Da) that acts on calcium and potassium mobilizing membrane mechanisms that affect the energy and motility properties of spermatozoa and inhibit their fertilizing capacity.

The active principle is a 20-amino acid water-soluble peptide that can be crystallized using freeze-drying techniques. The active principle can be included in a preparation for a topically used gel or combined in an oily formulation to be added to condoms.

Consequently, the active agent of the present invention affects the fertilizing potential without altering the integrity of the cell membrane. The active principle acts as a pharmacological agent that inhibits the capacitive response of the mature ejaculated spermatozoid and transforms such spermatozoid in a non-fertilizing gamete.

DETAILED DESCRIPTION OF THE INVENTION

The present invention is directed to an active agent with contraceptive properties. Said active agent corresponds to a molecular fraction of the venom from the spider *Latrodectus mirabilis*. In particular, the active agent is a peptide with a sequence according to SEQ ID NO 1 or sequences that are at least 85% similar, obtained by chemical synthesis or through recombinant DNA technologies.

In a preferred embodiment, the active agent with contraceptive properties is a peptide with 10 to 30 amino acids, preferably 20 amino acids. Said embodiment is exemplified by the sequence identified as SEQ ID NO 2 or sequences that are at least 85% similar, obtained by chemical synthesis or through recombinant DNA technologies.

The native structure of the venom from *Latrodectus mirabilis* has a high molecular weight (7843 Da, SEQ ID NO 1) and has three cysteine bridges (as shown in FIG. 1, which shows the native peptide in top and the designed analogous peptide). Said structure rends the native peptide biotechnologically inefficient to be transformed into a drug, due to the inherent problems of protein folding and correct formation of disulfide bridges. Due to the above, the fragment comprising the active principle was isolated and the cysteine in position 43 was replaced by an alanine, thus removing the disulfide bridge to obtain a "linear" peptide.

The designed analog has a linear quaternary and secondary structure. The distribution of electric charges on the molecular surface of the modified peptide (SEQ ID NO 2) is such that adhesion to cellular membranes is very efficient, which enables it to affect 100% of the spermatozoids at maximal doses (FIG. 2). Cell membranes have receptors or ionic channels that are sensitive to the binding of drugs, in which the main molecule has an electric charge (due to depolarization induced by the opening of channels).

In another preferred embodiment, the use of the spermicidal active agents is also considered for the preparation of a composition used as a lubricant and spermicide in condoms, in vaginal ovules, contraceptive sponges, vaginal lubricant gels and diaphragms, vaginal film or pressurized gels and topical creams.

The composition that comprises the active agent also comprises a gel component to be added to condoms in the internal side thereof or a gel-sol in the form of an ovule to dissolve in the vaginal duct at 37° C., among other ingredients.

The pharmaceutical composition that contains the peptides of the present invention can comprise one or more of the following pharmaceutically acceptable excipients or vehicles selected from: solvents, diluting agents, suspending agents, emulsifying agents, antioxidants, pharmaceutical preservatives, color agents, aromas, vehicles, excipient oily bases such as: water, glycerin, propylene glycol, hydroxyethylcellulose, diazolidinyl urea, monosodium phosphate, triethanolamine, carcomer, polyacrylic acid, disodium phosphate, propylparaben, methylparaben, and the like.

The previous excipient list is provided only with illustrative purposes and does not intend to limit the scope of the invention, where the active principle of the spermicide corresponds to the peptides of the invention, as described in the annexed claims.

APPLICATION EXAMPLES

Example A

Obtainment of the Active Principle with Spermicidal Activity from the Latrodectus mirabilis Venom In order to obtain the venom, venom glands containing the venomous extract have to be extracted from *Latrodectus mirabilis* spiders, which contain from 2 to 4 µL of venom per gland. For this effect, the animals were sacrificed by subjecting them to a cold shock with dry ice. The glands are extracted from the chelicerae, which are the structure that carry those glands. The glands are aliquoted inside 2.5-ml Eppendorf tubes with 200 µL of distilled water in a cold environment (−4° C.). The biological material obtained in this way is stored in an airtight container in a cold room (−20° C.) to be subsequently conducted to the fractioning and freeze-drying process.

The purification of the crude extract was performed by subjecting the crude *Latrodectus mirabilis* venom to chromatography on Sephadex G-50, with 85% recovery, and each pool was labeled as Arachnotoxin=Atx 1, 2, 3, 4. Subsequently, the fractions were subjected to a second chromatography through an HPLC column. Peaks were separated and their content was freeze-dried. The yield was calculated as the mg obtained in each fraction per each 100 mg of crude venom used in the purification. In the purification of peptides, a preparative Waters chromatography system (model Delta Prep 4000) was used, coupled to a UV-VIS detector (model 486), a fraction collector Pharmacia LKB-Frac-200 and a registering module Servogor 120.

The used experimental settings were:

Column: Vydac C18 (10×250 mm), 300 Å, 150 μm

Solvents: A: 0.1% TFA/$H_2O$

B: 0.1% TFA-60% ACN/$H_2O$

Gradient: 1-61% B in 60 minutes

Flow: 10 mL/min

Detection wavelength: 220 nm

In the fraction identified as F50, obtained in the chromatographic profile, a 7850 Da fragment was isolated, which was purified and sequenced, delivering a sequence of 69 amino acids (SEQ ID NO 1). This 69-amino acid chain was analyzed with BLAST and it presented a high similitude with the terminal chain of α-latrotoxin obtained from the spider *Latrodectus tredecimguttatus*. With the terminal 20-amino acid fragment, from Ser41 to Lys52 (highly conserved portion) a peptide analog was constructed replacing the cysteine in position 43 by an alanine, thus removing the disulfide bridge to obtain a "linear" peptide.

The peptides used in this work were manually synthesized using solid phase synthesis. For this method, the strategies t-Boc and Fmoc were used on resins MBAR, BAR and Rink as solid supports. Couplings were performed using an excess of 2.5 times of Boc-aa and DIC/HOBt in DCM/DMF (1:1 by volume) for 1 hour and monitored using the Kaiser test. Recoupling, when necessary, was performed using an excess of 2.5 times of Boc-aa and TBTU and 7 or BOP with excess of DIEA (pH between 8.0-9.0) in DMSO/NMP (1:4 by volume) for 1 hour. When necessary, during the general synthesis, three successive recouplings were performed, followed by a positive ninhydrin test. Finally, the peptidyl-resin was subjected to an acetyl reaction with acetic anhydride in DMF (1:4 by volume) for 20 minutes.

Example B

Determination of the Spermicidal Effect of the Wild-Type Peptide of SEQ ID NO 1 in Human Spermatozoa The spermicidal effect of the wild-type peptide and the constructed analog was assayed by assessing the sperm motility in human spermatozoa. For this, 15 mL of HTF-0.1% BSA medium (0.02 g BSA in 20 mL HTF) and 3 mL of HTF-1% BSA medium (0.04 g BSA in 4 mL HTF) were placed in an assay tube and incubated at 37° C. Subsequently, a sample of 2.6 mL of human semen was incubated during 25 minutes until liquefaction. Once liquefied, the sample was divided into 3 15-mL conical tubes with 2 mL of warm HTF-0.1% BSA in each tube. 860 μL of liquefied semen were vertically added to the bottom of each tube, gently pipetting to homogenize the mixture avoiding the formation of bubbles. Large clots were removed. Subsequently, the sample was centrifuged for 8 minutes at 1,800 rpm and the supernatant was discarded by touching only the surface of the medium with the pipette tip just on the tube walls and pipetting out the liquid. The pellet was resuspended in 3 mL of HTF-0.1% BSA, disgregated and subsequently centrifuged for 10 minutes at 1,800 rpm, then removing the supernatant. The pellet thus obtained was resuspended in 1 mL of warm HTF-1% BSA with the tube in vertical position and gently adding the medium. Next, the preparation was incubated for 1 hour at 37° C. with the tube inclined at a 45° angle (swim up). Once this stage was completed, the spermatozoid cloud was removed and the supernatants were combined and then centrifuged for 8 minutes at 1,800 rpm, discarding the supernatant. Then, spermatozoa were counted, reaching values around 10 million of selected spermatozoa per mL ($10\times10^6$/mL). Different concentrations of the total venom and the different venom fractions obtained in the chromatographic purification, as well as the constructed analog peptide, were applied to samples of the spermatozoid previously selected and counted and were incubated in HTF medium for 45 minutes at 37° C. A drop of the sample was extracted and placed on a microscope slide warmed to 36-37° C. and a slide cover warmed to the same temperature was placed on the sample. The sample was observed under the microscope with a 400× enlargement, always kept on the heated plate. An entire field was scrutinized and the spermatozoa that progressively move in a straight line and cross the observation field were subjectively valued. The spermatozoa that turn in circles or move forward in an oscillatory pathway are considered as abnormally moving spermatozoa. The percentage indicated (in FIG. 2) is the percentage of spermatozoa with no progressive linear movement with regard to the total number of accepted spermatozoa, being 50% the minimum acceptable, versus the logarithm of the concentration of spermicidal agent used in the experiment (log ATX: total venom, constructed analog or chromatographic fractions of the venom; F47, F48, F50).

Example C

Chemical Synthesis of the Active Peptide

The peptides were synthesized using t-Boc-type chemical synthesis, which consists in developing a temporal protecting group for N-α-amino groups, i.e. a labile acyl-tert-butyloxycarbonyl group, and protecting groups for lateral chains derived from the benzyl group (Bzl) that are resistant to weak acids (trifluoroacetic acid; TFA) and are removed by strong acids such as hydrogen fluoride (HF). In the t-Boc strategy, deprotection of the N-α-amino groups is performed with a gradient of TFA in dichloromethane (DCM) from 30 to 50% and a subsequent neutralization with 5% TEA (tetraethylammonium) in DCM (dichloromethane) to 10% DIPEA (N,N-diisopropylethylamine) in DCM. Deprotection of the N-α-amino groups was performed with 50% TFA in DCM and subsequent neutralization with 10% TEA. In the amino acid coupling step, the following reactants were used: BOP (benzotriazol-1-yloxy(trisdimethylammonium)phosphonium hexafluorophosphate) in the presence of DIPEA and TBTU (N,N,N',N'-tetramethyl-O-(benzotriazol-1-yl)uronium) in the presence of DIPEA. In all cases, an excess of 2.5 equivalents were used and the reaction time ranged from 1 to 2 hours. The solvent system used in the presence of DIC/HOBt was a mixture of 50% DCM in DMF (dimethylformamide), while for BOP/DIPEA or TBTU/DIPEA a mixture of 20% DMSO in NMP (N-methyl-pyrrolidone) was used. In case of failure of the third coupling alternative, the incorporated amino acid was acetylated. Acetylation consists in a reaction with 20% acetic anhydride in DMF plus 3 drops of Pyr for 20 minutes.

During the entire reaction course, Kaiser's test was used to monitor coupling and deprotection of the corresponding amino acids.

To release the peptide from the resin, protecting groups were removed from each amino acid by treatment with anhydrous HF at a concentration of 10 ml per gram of peptidyl-resin, using 10% anisol, dimethyl sulfate and thioanisol. Vacuum reservoirs and Teflon flasks were used for this task. The reaction occurs at 0° C. with constant stirring for 2 hours due to the large amount of arginine residues present in the peptide, and the process is repeated similarly for the TOS side-protecting group that is partially resistant to removal using HF. After the end of the reaction, the HF is removed by vacuuming and neutralization with a solution of 80 mg of sodium carbonate in 800 ml of deionized water. The peptide was washed with ether (g), which precipitates the resin, and the crude peptide was extracted with a solution of 5% and 50% acetic acid in water.

Next, the peptides were cyclezed to form disulfide bridges. The equipment used for this step is a 3-L 3-mouthed rounded-bottom flask. The crude peptide is dissolved in 400 ml of deionized water using a magnetic stirrer, an oxygen pump and a pH-meter. The solution is aerated for 72 hours in a cold room at 8-10° C. at a constant pH of 7.0. Cyclization efficiency is followed by RP-HPLC assessment.

Finally, the peptide was freeze-dried, purified and characterized by HPLC.

Example D

Production of a Spermicidal Peptide (Ac-[Ala$^{43}$]-ATX$_{41-60}$-NH$_2$) Using Recombinant DNA Technology The spermicidal peptide Ac-[Ala$^{43}$]-ATX$_{41-60}$-NH$_2$ (MW 2387.72 Da) has a known amino acid sequence (SEQ ID NO 2), which allows knowing the DNA sequence codifying for such peptide (SEQ ID NO 4). It is possible to assemble the sequence by conventional DNA oligonucleotide synthesis methods, and the restriction sites corresponding to a plasmid vector that is used for subcloning can also be introduced by using these synthesis methods. For example, plasmid vectors pF25 A and F allow expressing the peptide in the Sf21 insect cell line or in BL21 Codon Plus bacteria, obtained from PROMEGA Corp. USA.

The obtained peptide can be purified using the conventional HPLC method to isolate the peptide and get the required amounts according to the product's demand.

Example E

Production of the Native Peptide Using Recombinant DNA Technology

The wild-type peptide (MW 7843.70 Da) has a known amino acid sequence (SEQ ID NO 1), which allows knowing the DNA sequence codifying for such peptide (SEQ ID NO 3). It is possible to assemble the sequence by conventional DNA oligonucleotide synthesis methods, and the restriction sites corresponding to a plasmid vector that is used for subcloning can also be introduced by using these synthesis methods. For example, plasmid vectors pF25 A and F allow expressing the peptide in the Sf21 insect cell line or in BL21 Codon Plus bacteria, obtained from PROMEGA Corp. USA.

The obtained peptide can be purified using the conventional HPLC method to isolate the peptide and get the required amounts according to the product's demand.

Example F

Decrease of the Fertilizing Capacity of Spermatozoa in the Presence of Total *Latrodectus mirabilis* Venom and the Constructed Analog The decrease of the fertilizing capacity of human spermatozoa was assayed using penetration assays in hamster oocytes according to the protocol initially described by Yanagimachi et al. (1976). Briefly, golden hamster oocytes were collected; their striated membrane was removed, and oocytes were subsequently incubated with previously capacitated human spermatozoa at a concentration of $10^7$ spermatozoa/ml. The incubation was prolonged for 3-6 hours. Later, the oocytes were washed to remove spermatozoids that did not penetrate them and then fixed and stained with orcein. The oocytes were observed using phase contrast microscopy and were only considered to have been penetrated by spermatozoa when they contained a head in decondensation stage or a male pronucleus inside their cytoplasm.

Example G

Pharmaceutical Composition for Topical Application of the Spermicide of the Invention

| Ingredient | % by weight |
| --- | --- |
| Peptide according to SEQ ID NO 2 | 0.00365 |
| Benzoic acid | 0.8 |
| Propylparaben | 0.02 |
| Sorbic acid | 0.05 |
| Chlorocresol | 0.075 |
| Vaselin | 99.05 |

Sequences

SEQ ID NO 1:
ZDSLDPAEFACADDIDQAELLKNNDICLQCEDLHKEGLVFSLCKTNCFST
EYFQHCVKDLEEAKKEPPE

SEQ ID NO 2:
SLAKTNCFTTEYFQHCVKDL

SEQ ID NO 3:
taagatagcctggatccggcggaatttgcgtgcgcggatgatattgatca
ggcggaactgctgaaaaacaacgatatttgcctgcagtgcgaagatctgc
ataaagaaggcctggtgtttagcctgtgcaaaaccaactgctttagcacc
gaatattttcagcattgcgtgaaagatctggaagaagcgaaaaaagaacc
gccggaa SEQ ID NO 4:
agcctggcgaaaaccaactgctttaccaccgaatattttcagcattgcgt
gaaagatctg

---

The invention claimed is:

1. An isolated contraceptive peptide comprising the amino acid sequence of SEQ ID NO: 2.

2. A pharmaceutical contraceptive composition wherein said composition comprises at least one peptide according to claim 1 and one or more pharmaceutically acceptable vehicles.

3. The pharmaceutical composition according to claim 2 wherein said pharmaceutical vehicles are selected from the group consisting in solvents, diluting agents, suspending agents, emulsifying agents, antioxidants, pharmaceutical preservatives, coloring agents, scenting agents, vehicles, oily bases, excipients such as: water, glycerin, propylene glycol, hydroxyethylcellulose, diazolidinyl urea, monosodium phosphate, triethanolamine, carcomer, polyacrylic acid, disodium phosphate, and propylparaben, methylparaben.

4. The composition according to claim 2, wherein said composition is a spermicide.

5. A pharmacological composition comprising the contraceptive peptide according to claim 1, wherein the composition has contraceptive activity.

6. The composition according to claim 5 wherein said composition is a spermicide.

7. The composition according to claim 5, wherein said peptide has spermicidal activity.

8. The contraceptive peptide according to claim 1, wherein said peptide has spermicidal activity.

9. The contraceptive peptide according to claim 1, wherein said peptide inhibits sperm motility.

10. The contraceptive peptide according to claim 1, wherein said peptide is a linear peptide.

* * * * *

```
                        SEQUENCE LISTING

<160> NUMBER OF SEQ ID NOS: 6

<210> SEQ ID NO 1
<211> LENGTH: 69
<212> TYPE: PRT
<213> ORGANISM: Latrodectus mirabilis

<400> SEQUENCE: 1

Glx Asp Ser Leu Asp Pro Ala Glu Phe Ala Cys Ala Asp Asp Ile Asp
1               5                   10                  15

Gln Ala Glu Leu Leu Lys Asn Asn Asp Ile Cys Leu Gln Cys Glu Asp
            20                  25                  30

Leu His Lys Glu Gly Leu Val Phe Ser Leu Cys Lys Thr Asn Cys Phe
        35                  40                  45

Ser Thr Glu Tyr Phe Gln His Cys Val Lys Asp Leu Glu Glu Ala Lys
    50                  55                  60

Lys Glu Pro Pro Glu
65

<210> SEQ ID NO 2
<211> LENGTH: 20
<212> TYPE: PRT
<213> ORGANISM: Artificial Sequence
<220> FEATURE:
<223> OTHER INFORMATION: Spermicidal Peptide

<400> SEQUENCE: 2

Ser Leu Ala Lys Thr Asn Cys Phe Thr Thr Glu Tyr Phe Gln His Cys
1               5                   10                  15

Val Lys Asp Leu
            20

<210> SEQ ID NO 3
<211> LENGTH: 207
<212> TYPE: DNA
<213> ORGANISM: Latrodectus mirabilis

<400> SEQUENCE: 3
taagatagcc tggatccggc ggaatttgcg tgcgcggatg atattgatca ggcggaactg      60
```

```
ctgaaaaaca acgatatttg cctgcagtgc gaagatctgc ataaagaagg cctggtgttt    120
agcctgtgca aaaccaactg ctttagcacc gaatattttc agcattgcgt gaaagatctg    180
gaagaagcga aaaaagaacc gccggaa                                        207

<210> SEQ ID NO 4
<211> LENGTH: 60
<212> TYPE: DNA
<213> ORGANISM: Artificial Sequence
<220> FEATURE:
<223> OTHER INFORMATION: Nucleotide Sequence Encoding Spermicidal
      Peptide

<400> SEQUENCE: 4
agcctggcga aaaccaactg ctttaccacc gaatattttc agcattgcgt gaaagatctg    60

<210> SEQ ID NO 5
<211> LENGTH: 24
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (11)..(11)
<223> OTHER INFORMATION: Xaa = cysteine having an acetamidomethyl (ACM)
      protecting group

<400> SEQUENCE: 5

Glx Asp Ser Leu Asp Pro Ala Glu Phe Ala Xaa Ala Asp Asp Ile Asp Gln
1               5                   10                  15

Ala Glu Leu Leu Lys Asn Asn
        20

<210> SEQ ID NO 6
<211> LENGTH: 34
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (23)..(23)
<223> OTHER INFORMATION: Xaa = cysteine having an acetamidomethyl (ACM)
      protecting group

<400> SEQUENCE: 6

Asp Ile Cys Leu Gln Cys Glu Asp Leu His Lys Glu Gly Leu Val Phe
1               5                   10                  15

Ser Leu Cys Lys Thr Asn Xaa Phe Ser Thr Glu Tyr Phe Gln His Cys
            20                  25                  30

Val Lys
```